（12）United States Patent
Rasch-Menges et al.

(10) Patent No.: US 8,066,958 B2
(45) Date of Patent: Nov. 29, 2011

(54) DEVICE AND KIT FOR CALIBRATING BODILY FLUID SAMPLING DEVICES

(75) Inventors: Juergen Rasch-Menges, Schwetzingen (DE); Paul Jansen, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1146 days.

(21) Appl. No.: 11/753,217

(22) Filed: May 24, 2007

(65) Prior Publication Data

US 2007/0239068 A1 Oct. 11, 2007

Related U.S. Application Data

(63) Continuation of application No. 11/536,938, filed on Sep. 29, 2006, now abandoned, which is a continuation of application No. 11/276,095, filed on Feb. 14, 2006, now abandoned, which is a continuation of application No. 11/153,854, filed on Jun. 15, 2005, now abandoned, which is a continuation of application No. 10/960,451, filed on Oct. 7, 2004, now abandoned, which is a continuation of application No. 10/728,037, filed on Dec. 4, 2003, now abandoned, which is a continuation of application No. PCT/US02/18186, filed on Jun. 10, 2002, now abandoned.

(51) Int. Cl.
*G01N 31/00* (2006.01)
*B01L 3/00* (2006.01)

(52) U.S. Cl. ...... 422/430; 15/244.1; 15/244.4; 422/500; 422/558; 436/8; 436/11; 436/12; 436/13; 436/14; 436/15; 436/16; 436/19

(58) Field of Classification Search ............... 422/61, 422/430, 500, 558; 436/8, 11–16, 19; 401/23, 401/130, 139, 202, 207, 262; 118/264, 270; 15/97.2, 244.1, 244.4

See application file for complete search history.

(56) References Cited

U.S. PATENT DOCUMENTS

| | | | | | |
|---|---|---|---|---|---|
| 3,449,081 A | * | 6/1969 | Hughes | | 422/61 |
| 3,610,248 A | * | 10/1971 | Davidson | | 606/236 |
| 3,878,831 A | * | 4/1975 | Zackheim | | 600/575 |
| 3,892,058 A | * | 7/1975 | Komatsu et al. | | 53/425 |
| 3,999,505 A | | 12/1976 | Kato et al. | | |
| 4,014,322 A | * | 3/1977 | Shah | | 600/573 |
| 4,078,892 A | * | 3/1978 | Steinbrink, Jr. | | 436/97 |

(Continued)

FOREIGN PATENT DOCUMENTS

EP 0 520 443 12/1992

(Continued)

*Primary Examiner* — Arlen Soderquist
(74) *Attorney, Agent, or Firm* — Woodard, Emhardt, Moriarty, McNett & Henry LLP

(57) ABSTRACT

A control solution packet for calibrating a bodily fluid sampling device includes a container, a control solution pressurized within the container, and a membrane for covering and sealing the container. The control solution can be pressurized before or during calibration so as to ensure the appropriate amount of control solution is delivered to the bodily fluid sampling device. The control solution is manufactured to have a viscosity that controls delivery of the control solution to the device. The membrane is permeable by a piercing device of the bodily fluid sampling device and seals around the piercing device during calibration. In another aspect, the container is in the form of a capsule or dosing attachment that contains the control solution along with a sponge-like material.

8 Claims, 10 Drawing Sheets

U.S. PATENT DOCUMENTS

| | | | |
|---|---|---|---|
| 4,116,336 A * | 9/1978 | Sorensen et al. | 206/524.8 |
| 4,150,904 A * | 4/1979 | Stewart | 401/186 |
| 4,266,941 A * | 5/1981 | Sullivan | 436/68 |
| 4,289,648 A * | 9/1981 | Hoskins et al. | 436/11 |
| 4,368,746 A * | 1/1983 | Spatz | 401/202 |
| 4,418,702 A * | 12/1983 | Brown et al. | 600/573 |
| 4,468,271 A | 8/1984 | Pierson | |
| 4,559,052 A * | 12/1985 | Babson | 604/403 |
| 4,600,697 A * | 7/1986 | Smernoff | 436/174 |
| 4,635,467 A * | 1/1987 | Hoffa et al. | 73/1.04 |
| 4,637,403 A * | 1/1987 | Garcia et al. | 600/583 |
| 4,643,976 A * | 2/1987 | Hoskins | 436/15 |
| 4,654,127 A * | 3/1987 | Baker et al. | 205/792 |
| 4,747,720 A * | 5/1988 | Bellehumeur et al. | 401/205 |
| 4,790,979 A * | 12/1988 | Terminiello et al. | 422/56 |
| 4,847,050 A * | 7/1989 | Jenkins et al. | 422/102 |
| 4,872,956 A * | 10/1989 | Kotani et al. | 205/777 |
| 4,889,613 A * | 12/1989 | McNeal et al. | 204/416 |
| 4,960,708 A * | 10/1990 | Zowtiak et al. | 436/11 |
| 4,961,661 A * | 10/1990 | Sutton et al. | 401/6 |
| 4,983,061 A * | 1/1991 | Demarest | 401/148 |
| 5,000,193 A * | 3/1991 | Heelis et al. | 600/573 |
| 5,004,583 A * | 4/1991 | Guruswamy et al. | 422/58 |
| 5,042,690 A * | 8/1991 | O'Meara | 222/83 |
| 5,084,245 A * | 1/1992 | Berke et al. | 422/61 |
| 5,145,565 A * | 9/1992 | Kater et al. | 600/341 |
| 5,233,860 A * | 8/1993 | Mori et al. | 73/19.1 |
| 5,243,982 A * | 9/1993 | Mostl et al. | 600/316 |
| 5,279,294 A * | 1/1994 | Anderson et al. | 600/322 |
| 5,299,877 A * | 4/1994 | Birden | 401/206 |
| 5,332,121 A * | 7/1994 | Schmidt et al. | 222/95 |
| 5,352,410 A * | 10/1994 | Hansen et al. | 422/58 |
| 5,393,391 A * | 2/1995 | Dietze et al. | 205/781.5 |
| 5,395,365 A * | 3/1995 | Weiler et al. | 604/415 |
| 5,405,001 A * | 4/1995 | Lillard | 206/221 |
| 5,421,981 A * | 6/1995 | Leader et al. | 204/403.13 |
| 5,555,673 A * | 9/1996 | Smith | 47/1.5 |
| 5,582,184 A * | 12/1996 | Erickson et al. | 600/576 |
| 5,582,696 A * | 12/1996 | Sheehan | 204/403.06 |
| 5,780,302 A * | 7/1998 | Conlon et al. | 436/8 |
| 5,857,983 A | 1/1999 | Douglas et al. | |
| 5,913,232 A * | 6/1999 | Betts et al. | 73/1.03 |
| 5,951,492 A | 9/1999 | Douglas et al. | |
| 5,964,718 A | 10/1999 | Duchon et al. | |
| 6,099,484 A * | 8/2000 | Douglas et al. | 600/583 |
| 6,152,889 A | 11/2000 | Sopp et al. | |
| 6,203,504 B1 | 3/2001 | Latterell et al. | |
| 6,412,997 B2 * | 7/2002 | Berke et al. | 401/6 |
| 6,451,606 B1 * | 9/2002 | Konig et al. | 436/8 |
| 6,685,691 B1 * | 2/2004 | Freund et al. | 604/403 |
| 6,706,000 B2 * | 3/2004 | Perez et al. | 600/583 |
| 6,706,159 B2 * | 3/2004 | Moerman et al. | 204/403.03 |
| 6,887,709 B2 * | 5/2005 | Leong | 436/8 |
| 7,025,774 B2 * | 4/2006 | Freeman et al. | 606/181 |
| 7,264,627 B2 * | 9/2007 | Perez | 606/181 |
| 7,303,726 B2 * | 12/2007 | McAllister et al. | 422/68.1 |
| 7,749,453 B2 * | 7/2010 | Rannikko et al. | 422/102 |
| 7,803,123 B2 * | 9/2010 | Perez et al. | 600/583 |
| 2003/0211616 A1 * | 11/2003 | Leong | 436/8 |

FOREIGN PATENT DOCUMENTS

| | | |
|---|---|---|
| JP | 03/146068 | 6/1991 |
| WO | 02/100265 | * 12/2002 |

* cited by examiner

DEVICE AND KIT FOR CALIBRATING BODILY FLUID SAMPLING DEVICES

REFERENCE TO RELATED APPLICATIONS

This application is a continuation of U.S. Utility patent application Ser. No. 11/536,938 filed Sep. 29, 2006, now abandoned which is a continuation of U.S. Utility patent application Ser. No. 11/276,095 filed Feb. 14, 2006, now abandoned which is a continuation of U.S. Utility patent application Ser. No. 11/153,854 filed Jun. 15, 2005, now abandoned which is a continuation of U.S. Utility patent application Ser. No. 10/960,451 filed Oct. 7, 2004, now abandoned which is a continuation of U.S. Utility patent application Ser. No. 10/728,037 filed Dec. 4, 2003, now abandoned which is a continuation of International Patent Application No. PCT/US02/18186 filed Jun. 10, 2002, published in English, now abandoned which are hereby incorporated by reference in their entirety.

BACKGROUND OF THE INVENTION

The present invention generally relates to methods and devices for the calibration of a bodily fluid sampling device, and more specifically, but not exclusively, concerns a control solution packet for delivery of a control solution to a bodily fluid sampling device.

The need for simple methods to determine the biological and chemical constituents in bodily fluids has increased as point of care testing has gained in popularity. A common application is the self-monitoring of blood glucose concentrations by patients with diabetes. These patients frequently administer insulin or take other therapeutic actions based on the test results. As testing is generally recommended multiple times daily and may occur in any setting, an easy to use and relatively inexpensive method to accomplish this task is required. Self-administered bodily fluid sampling devices, such as glucose meter devices, are typically used to perform such testing.

Bodily fluid monitoring devices can collect a blood sample, or other bodily fluid samples, in a number of ways. For instance, in one less traumatic technique, a glucose monitoring device having a small hollow needle or lancet is used to pierce the patient's skin. The device is pressed against the skin to force a small sample of the monitored bodily fluid, such as blood or interstitial fluid, up the needle and into a testing area of the device. Once in the testing area, the fluid sample can be analyzed using any one of a number of techniques, such as using a chemically reactive test strip, measuring the sample's electrical properties or measuring the optical properties of the sample (i.e., infrared analysis). Examples of such devices are disclosed in U.S. Pat. Nos. 6,203,504, issued to Latteral et al. on Mar. 20, 2001, and 6,152,889, issued to Sopp et al. on Nov. 28, 2001, which are hereby incorporated by reference in their entirety.

With the advent of home testing, the bodily fluid sampling device and associated disposables have to be periodically tested to ensure that both are providing accurate test results. Typically, the bodily fluid sampling device is calibrated by loading a calibration strip into the device. Inaccurate calibration readings may result when the user fails to follow the proper testing procedures.

If the user feels that the disposable test strips are not providing an accurate reading, then the accuracy of the disposable test strips can be tested utilizing a control solution that has a known value. For example, a liquid control solution may be applied to a test strip which is then inserted into the meter.

In order to utilize a control solution, the user is therefore required to perform a plurality of steps, any of which can lead to the introduction of errors in the control solution testing, thereby potentially leading to erroneous results. Moreover, by not calibrating the device in the manner in which it is used, problems associated with the operation of the device, such as contamination, may remain undetected.

Therefore, there is a need for methods and devices that enable a user to easily and quickly perform a control test on a bodily fluid sampling device and that reduces or eliminates any chance of error occurring during the control test.

SUMMARY OF THE INVENTION

The present invention relates to an improved control solution packet for calibrating a bodily fluid sampling system includes a device and a disposable test strip in which the control solution packet provides easy and accurate test results.

According to one aspect of the present invention, there is provided a control solution packet for calibrating a bodily fluid sampling system, the control solution packet including a container, a control solution located within the container, and a membrane covering and sealing the container, wherein the membrane is permeable by a piercing device of the bodily fluid sampling device.

According to another aspect of the present invention, there is provided a control solution packet for calibrating a bodily fluid sampling system, the control solution device packet including a control solution, and a capsule having a membrane, wherein the membrane is permeable by a piercing device of the bodily fluid sampling device.

According to a further aspect of the present invention, a method is provided for using a control solution packet to calibrate a bodily fluid sampling device. The bodily fluid sampling device has a piercing device for piercing the skin to recover the bodily fluid. The control packet comprises a container, a control solution located within the container, and a membrane covering and sealing the container. The method includes the steps of placing the bodily fluid sampling device in contact with the control solution packet, advancing the piercing device to pierce the control solution packet, collecting a sample of the control solution, and reading the bodily fluid sampling device.

A further aspect of the present invention concerns a control solution packet that includes a container having at least a portion that is permeable by a piercing device of a bodily fluid sampling device. A control solution is sealed within the container, and the control solution is adapted to calibrate the bodily fluid sampling device. The control solution is pressurized to force at least some of the control solution into the bodily fluid sampling device.

In another aspect of the present invention, a calibration system includes a container and a membrane that covers at least part of the container. The membrane is permeable by a piercing device of a body fluid sampling device. A pressurized solution is contained within the container for calibrating the body fluid sampling device.

According to a further aspect of the present invention, a method is provided for calibrating a bodily fluid sampling device that has a piercing device. A control solution is provided within a permeable packet. The bodily fluid sampling device is placed against the permeable packet, and the packet is pierced with the piercing device. The solution is pressurized in the packet either prior to placing the sampling device against the packet, or as a result of pressing the sampling device against the packet. A sample of the control solution is collected from the packet. A value for the sample of the control solution is read with the bodily fluid sampling device, and the piercing device is removed from the packet.

A further aspect concerns an apparatus for calibrating a bodily fluid sampling device. The apparatus includes a container and a porous material provided in the container. A control solution is provided in the porous material, and the control solution is adapted to calibrate the bodily fluid sampling device. The porous material is compressible to pressurize the control solution and dispense the control solution to the bodily fluid sampling device when the porous material is compressed.

Another aspect concerns a method for calibrating a bodily fluid sampling device. The method includes placing the bodily fluid sampling device in contact with a container that contains a control fluid. A sample of the control fluid is transferred from the container to a test area inside the bodily fluid sampling device. A value for the sample of the control fluid is read with the bodily fluid sampling device.

Other forms, embodiments, objects, features, advantages, benefits and aspects of the present invention shall become apparent from the detailed drawings and description contained herein.

DESCRIPTION OF SELECTED EMBODIMENTS

Figure 1:
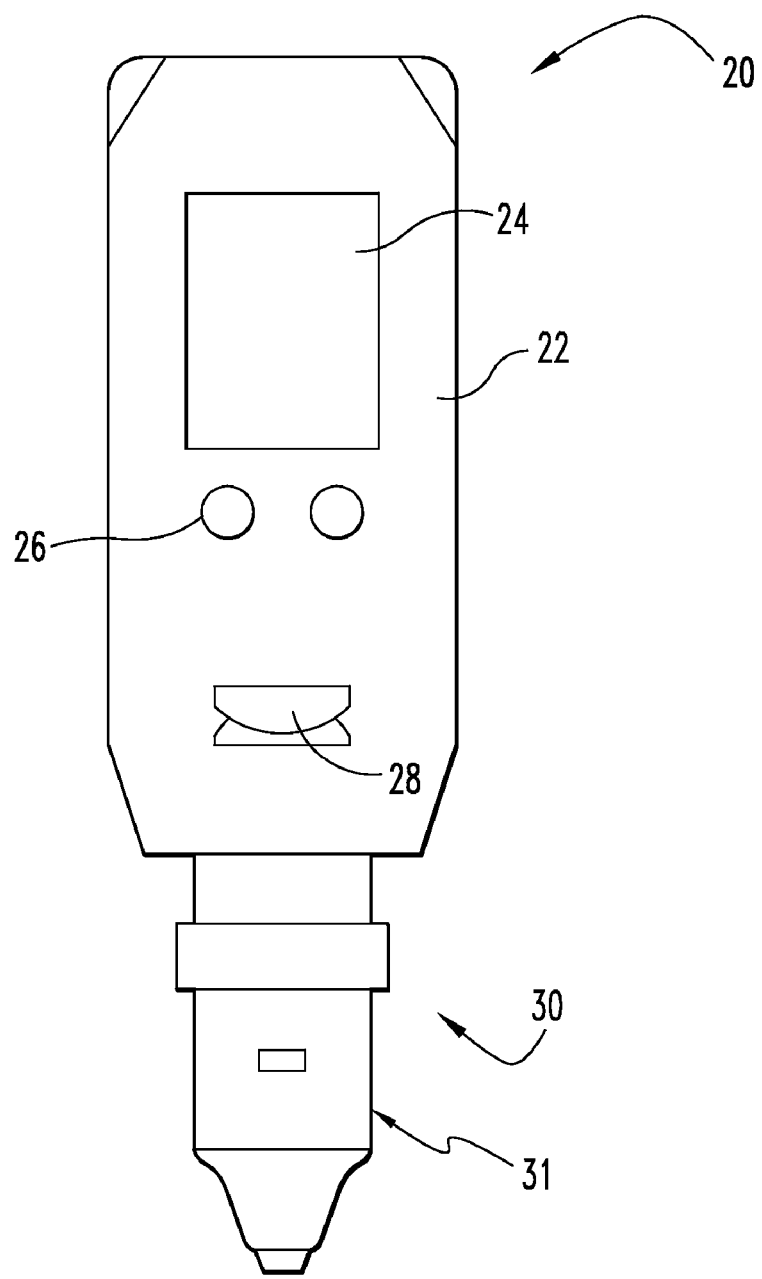
FIG. 1 is a front elevational view of a pressure-type, bodily fluid sampling device useful with the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the art that some of the features which are not relevant to the invention may not be shown for the sake of clarity.

The present invention concerns systems and techniques for calibrating bodily fluid sampling devices. In one aspect, the invention concerns a control solution packet for calibrating "pressure-type" bodily fluid sampling devices, which are designed to receive samples of bodily fluid under pressure. The control solution packet has a container that stores a control solution that is either pressurized or able to be pressurized during calibration. During calibration, a piercing device of a bodily fluid sampling device pierces the container and a sample of the control solution is removed for a reading. In one embodiment, the control solution is pre-pressurized in the container, and in another embodiment, the packet is pressurized by compressing the packet. The control solution is pressurized so as to control the amount of control solution delivered to the bodily fluid sampling device. If too little or too much of the control solution is delivered, then errors in the calibrated reading can occur. Further, a parameter of the control solution, such as viscosity of the solution, can be selected to control the amount of solution delivered to the device.

In order to prevent leakage of the control solution around the piercing device, the control solution packet can further include a permeable membrane that covers the portion of the container that is pierced by the piercing device. To further control the amount of control solution delivered to the bodily fluid sampling device, the control solution packet can include a porous sponge and/or other foam material.

In another aspect, the invention concerns a dosing attachment used to calibrate a bodily fluid sampling device. The dosing attachment is adapted to couple to a standard control solution bottle that contains the control solution. The bottle is squeezed to transfer a dose of the control solution to a collection portion in the dosing attachment. Once the collection portion is filled with the control solution, the collection portion is squeezed to wet a porous sponge-like material with the control solution. To calibrate the bodily fluid sampling device, the control fluid is delivered to a test area inside the bodily fluid sampling device by pressing the porous sponge-like material against the test area. A calibration reading is taken from the control solution sample deposited on the test area.

Figure 2:
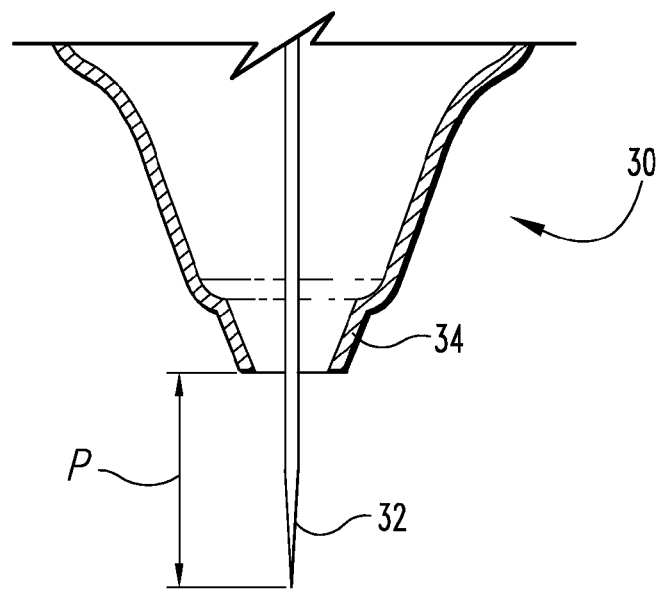
FIG. 2 is a partial, cross-sectional view of a sampling system in the FIG. 1 bodily fluid sampling device.

In FIGS. 1 and 2, there is illustrated a pressure-type bodily fluid sampling (testing) device or meter 20 that can be calibrated with the control solution packet of the present invention. The bodily fluid sampling device 20 includes a main body 22, a display 24, at least one button 26, and a calibration chip interface 28. Button 26 is used to operate the bodily fluid sampling device 20. The device 20 further includes a sampling system 30, which includes a test area 31. The test area 31 is where the bodily fluid sample is tested, and the display 24 displays the results from the test. As will be appreciated, the test area 31 can include a chemically reactive test strip, electrical sensors, optical sensors and/or other types of bodily fluid testing systems that are able to determine the constituents of bodily fluids.

As shown in FIG. 2, the sampling system 30 includes a piercing device or member 32 surrounded by a ring-shaped member 34. When a sample is taken, the ring-shaped member 34 is pressed against the patient's skin to create a local pressurized area of bodily fluid under the skin. The piercing device 32 can be a lancet, needle, or a similar instrument. A lancet is generally a sharp pointed and commonly 2-edged surgical instrument used to make a small incision. However, if a lancet is used, a capillary tube, cannula or transfer membrane is needed to withdraw the control solution to the test area 31 of the bodily fluid sampling device 20. In comparison, the needle is generally a hollow instrument for removing material from the body such that the bodily fluid will flow through a lumen in the needle and to the test area 31 of the bodily fluid sampling device 20.

In use, the bodily fluid sampling device 20 is placed over an appropriate incision site, such as a forearm or finger tip. A force is then applied to press the bodily fluid sampling device 20 against the skin and the piercing device 32 is deployed to pierce the skin. FIG. 2 illustrates the piercing device 32 in the deployed position. The tip of the piercing device 32 penetrates the patient's skin, thereby creating a small incision having a penetration depth P typically 0.1 to 5 mm deep. By pressing the ring-shaped member 34 against the patient's skin, a localized area of high pressure is created that forces a sample of bodily fluid, such as blood and/or interstitial fluid, up through the piercing device 32 and into the test area 31 of the device 20. The bodily fluid sampling device 20 is then removed from the incision, and a reading of the fluid is then obtained.

Each bodily fluid sampling device 20 will have its own specific instructions for use and method of obtaining a reading. The present invention is designed to work with many types of bodily fluid sampling devices 20. For example, both U.S. Pat. Nos. 6,203,504, issued to Latteral et al. on Mar. 20, 2001, and 6,152,889, issued to Sopp et al. on Nov. 28, 2001, which are hereby incorporated by reference in their entirety, disclose other examples of bodily fluid sampling devices 20 that can be calibrated with the control solution packet of the present invention. It will be understood that the present invention is useful with any of the variety of bodily fluid sampling devices which receive the fluid based on the pressure of the fluid, such devices being referred to herein as pressure type bodily fluid sampling devices.

Test results obtained from bodily fluid sampling devices 20 may vary in both accuracy and precision. Therefore it is necessary to provide a monitoring agent or "control solution" which determines whether the bodily fluid sampling device is providing an accurate reading. Accordingly, it is important to test the sampling device 20 using a control solution which acts in a manner similar to the bodily fluid that is being tested. The control solution includes a fluid which will cause the sampling device 20 to display a known value. Therefore, if the sampling device 20 does not display the predetermined value, then it can be determined that the sampling device 20 is not operating properly.

Figure 3A:
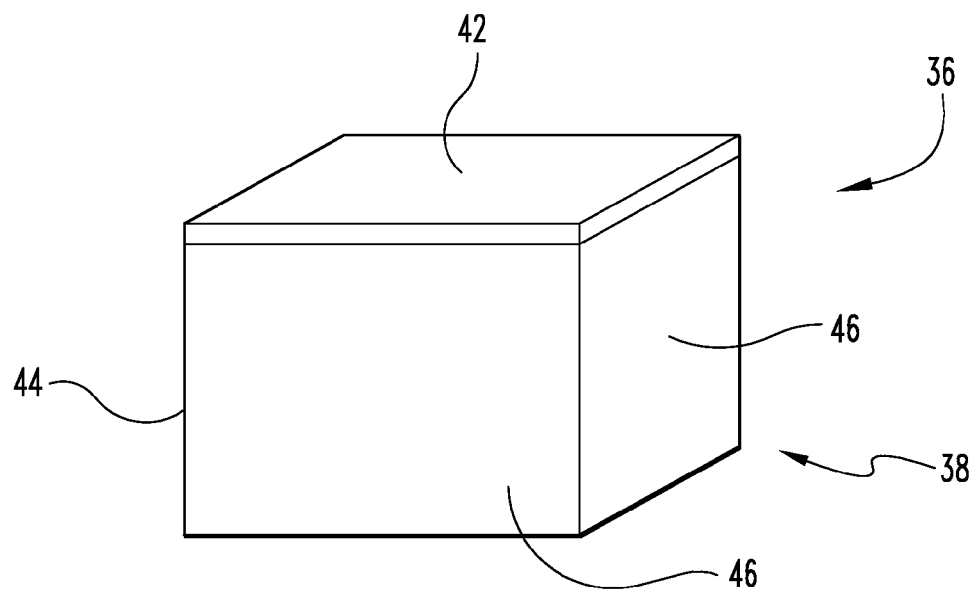
FIG. 3A is a perspective view of a control solution packet according to one embodiment of the present invention.
Figure 3B:
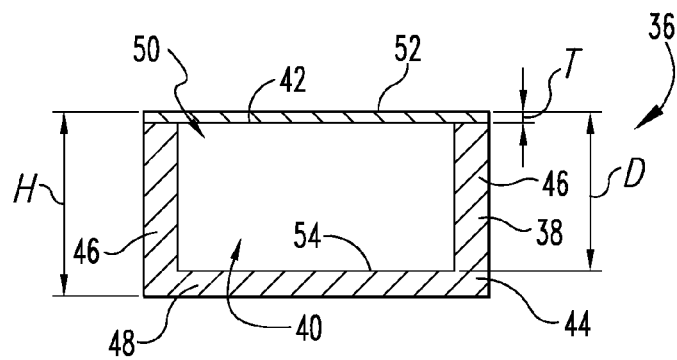
FIG. 3B is a cross-sectional view of the FIG. 3A control solution packet.

FIGS. 3A and 3B illustrate a control solution packet 36 according to one embodiment of the present invention that is used to calibrate a bodily fluid sampling device. The control solution packet 36 includes a container 38, a control solution or fluid 40 contained within the container 38, and a membrane 42 that covers and seals the container 38. As shown, the container 36 has container walls 44 that form the overall shape of the container 36. In the illustrated embodiment, the container walls 44 include sidewalls 46 and a base portion 48 spanning across and connecting one end of the sidewalls 46. At the other end, opposite the base portion 48, the sidewalls 46 define an opening 50 covered by the membrane 42. In one embodiment, the membrane 42 is sealed to the sidewalls 46 with glue. However, it should be appreciated that the membrane 42 can be attached to the sidewalls 46 in other manners as would occur to those generally skilled in the art. As shown in the FIG. 3A-B embodiment, the container 38 has a rectangular, cross-sectional shape. However, it can be appreciated that the container 38 can have other cross-sectional shapes, such as an oval shape, so long as the container 38 is able to hold the control fluid 40. In one embodiment, each control solution packet 36 is designed for a single or one time use. In another embodiment, the packet 36 is designed for multiple uses.

The packet 36 has an overall height H which is set according to each bodily fluid sampling device 20 so that the piercing device 32 penetrates only one side of the control solution packet 36. In particular, depth D of the container 36, which is the distance from top surface 52 of the membrane 42 to top surface 54 of the of the base portion 48, is greater than the penetration depth P (FIG. 2) of the bodily fluid sampling device 20 such that, even when the membrane 42 deflects due to any pressure exerted by the bodily fluid sampling device 20 during calibration, the base portion 48 is not penetrated by the piercing device 32. In one embodiment, the height H of the container 38, including the membrane 42, is between about 0.1 mm to about 10 cm. In addition, the height H of the container 38 will vary according to the penetration depth P of the bodily fluid sampling device 20 and the amount of control fluid 40 needed to obtain a sample sufficient for performing a control test. Furthermore, by controlling the penetration depth P by the piercing device 32 in the container 38, the control solution packet 36 prevents the bodily fluid sampling device 20 and control fluid 40 from becoming contaminated. In one embodiment, the container 38 is made of polyvinyl chloride. It should be appreciated, however, that the container can be made of other materials including plastic, glass, rubber and/or a synthetic type material, to name a few.

The control solution packet 36 according to the present invention allows pressure-type bodily fluid sampling devices 20 to be calibrated. At some point during calibration, the control fluid 40 is pressurized within the control solution packet 36 such that the pressurized control fluid 40 is forced into the pressure-type bodily fluid sampling device 20. The control fluid 40 can be pressurized such that the pressure of the control fluid 40 is higher than the surrounding atmospheric pressure during calibration of the bodily fluid sampling device 20. In one form of the present invention, the control fluid 40 is pre-pressurized within the control solution packet 36 during manufacture of the control solution packet 36.

In another form, the control fluid 40 is pressurized while the control fluid 40 is sampled during calibration. In this form, the control solution packet 36 is manufactured with the control fluid 40 sealed in the packet at generally around ambient pressure. The container walls 44 are generally rigid, while the membrane 42 is deformable so as to allow pressurization of the control fluid 40. During calibration, the downward pressure of the bodily fluid sampling device 20 on the membrane 42 pressurizes the control fluid 40 within the container 38, and the now pressurized control solution packet 36 forces the control fluid 40 up the piercing device 32 and into the test area 31 of the device 20.

The pressure within the control solution packet 36 will vary depending on requirements of the sampling device 20. The pressure of the control fluid 40 is pressurized high enough so as to fill the test area 31 of the device 20 with enough control fluid 40, while at the same time is not over pressurized so as to prevent flooding of the test area 31 in order to provide an accurate reading. Accordingly, the control solution packets 36 in one embodiment can have an internal pressure anywhere from ambient pressure to about 300 pounds per square inch (psi). In one embodiment, the internal pressure of the fluid is from above 0 pounds per square inch gauge (psig) to 20 psig, and more preferably from above 0 psig to 8 psig. The foregoing pressures apply whether pressurized ahead of time in the packet or if pressurized by pressing the fluid sampling device against the packet.

In another aspect of the present invention, the viscosity of the control fluid 40 in the control solution packet 36 is maintained so as to control the amount of control fluid 40 delivered to the test area 31 during calibration. In one form, the control fluid 40 simulates the viscosity of the bodily fluid being tested. If the viscosity of the control fluid 40 is too low, the control fluid 40 may flood the test area 31 with excessive solution, which reduces the precision of the measurement. Excess control fluid 40 within the bodily fluid sampling device 20 can also spread to contaminate the rest of the sampling device 40. On the other hand, if the viscosity is too high, none or too little of the control fluid 40 may reach the test area 31 and the device 20 would then provide inaccurate results. For instance, when the test area 31 incorporates a test strip, the rate of dispersion on the test strip and the volume of the control fluid 40 delivered to the test strip can be controlled through the viscosity of the control fluid 40. The viscosity of the control fluid 40 can further control the wetting of the test area 31. For example, as the control fluid 40 becomes more viscous, wetting of the test strip becomes slower. According to the present invention, the viscosity of the control fluid 40 is based on the volume of control fluid 40 that needs to be delivered to the test area 31, as well as the capacity to effectively wet the test area 31. In one embodiment, the control fluid 40 has a viscosity of between about 250 centipoise (cP) and about 25,000 cP. It can be appreciated, however, that the viscosity of the control fluid 40 can vary depending on requirements of the bodily fluid sampling device 20.

In another embodiment, alginic acid is added to the control fluid 40 to increase the viscosity of the control fluid 40. In one form, the control fluid 40 is combined with up to about 10% alginic acid. In another form, a control fluid 40 is combined with about 1% to about 5% alginic acid. The control fluid 40 can have properties specifically selected for the bodily fluid sampling device 20. As should be appreciated, the viscosity of the control fluid 40 can be modified using other techniques as would occur to those skilled in the art.

As discussed above, the membrane 42 is made of a permeable material that can be pierced by the piercing device 32 of the bodily fluid sampling device 20. In one aspect, during piercing, the membrane 42 provides a similar sensation to that of piercing human skin. When in use, the membrane 42 seals around the piercing device 32 to reduce leakage of the control fluid 40 from around the piercing device 32. Moreover, the membrane 42 assists in the retention of the shape of the control solution packet 36. In one embodiment, the membrane 42 is made from a deformable elastic material, which allows the membrane 42 to deflect to pressurize the control fluid 40. In one form, the membrane 42 is made of silicon tape. However, it should be understood that the membrane 42 can be made from other types of materials that can be pierced by the piercing device 32. By way of non-limiting example, the membrane 42 can be made from a foil and/or rubber, to name a few materials. Thickness T of the membrane 42 depends on many factors including, but not limited to, the material used to form the membrane 42, desired control solution pressure, control solution viscosity, and the bodily fluid sampling device type. In one embodiment, the thickness T of the membrane 42 is between about 0.0005 mm and about 5 mm.

Figure 4:
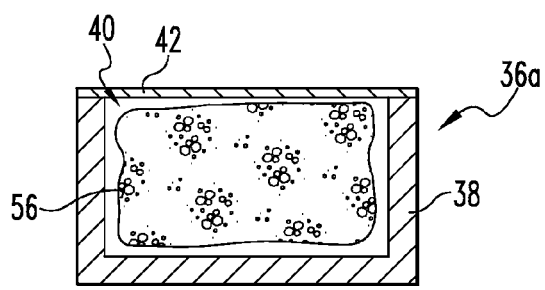
FIG. 4 is a cross-sectional view of a control solution packet according to another embodiment of the present invention.

A control solution packet 36a according to another embodiment of the present invention is illustrated in FIG. 4. Like the embodiment illustrated in FIG. 3, the FIG. 4 control solution packet 36a includes container 38, control fluid 40 located within the container 38, and permeable membrane 42 covering and sealing the container 38. In addition, the control solution packet 36a includes a porous, sponge/foam-like material 56 located within the container 38. With such a construction, material 56 regulates delivery of the control fluid 40 to the bodily fluid sampling device 20. The sponge-like material 56 resists deformation of the membrane 42 during the piercing of the control solution packet 36a so as to prevent over-pressurization of the control fluid 40. Moreover, the resistance provided by material 56 prevents excessive deformation of the membrane 42 which in turn helps to ensure that the piercing device 32 pierces through only one side of the package 36a. In one embodiment, material 56 includes a synthetic foam material. It should be understood that material 56 can include other types of resilient, porous materials.

Figure 5:
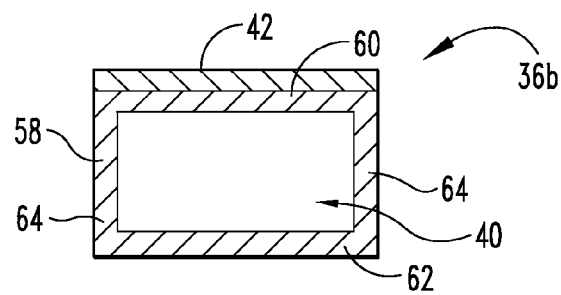
FIG. 5 is a cross-sectional view of a control solution packet according to a further embodiment of the present invention.

A control solution packet 36b according to a further embodiment of the present invention is illustrated in FIG. 5. In the illustrated embodiment, the control solution packet 36b includes a closed, permeable container 58 in which the control fluid 40 is contained. In container 58, the control fluid 40 is stored in a pressurized state. The container 58 is rigid and/or semi-rigid to resist the force imparted by the pressurized control fluid 40. As shown, the closed container 58 has a generally rectangular cross-sectional shape and includes a membrane wall portion 60 and an opposite base wall portion 62 connected together through opposing sidewalls 64. At one side of package 36b, membrane 42 is secured to the membrane wall portion 60 of the closed container 58. The closed container 58 is formed from a material that is permeable by the piercing device 32. During calibration, the piercing device 32 of the bodily fluid sampling device 20 pierces through both the membrane 42 and the membrane wall portion 60. The membrane 42 seals around the piercing device 32 to control leakage of the control fluid 40 from around the piercing device 32.

Figure 6:
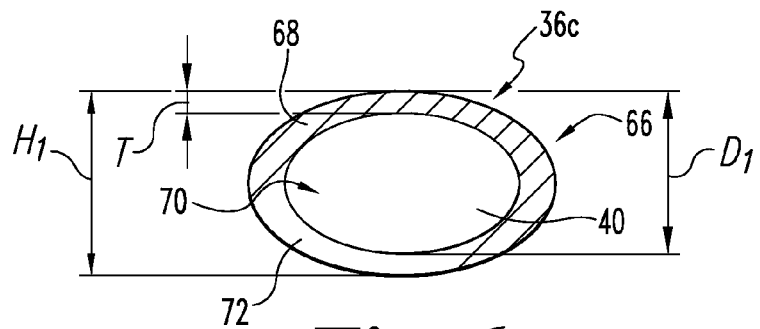
FIG. 6 is a cross-sectional view of a control solution packet according to an alternative embodiment of the present invention.

FIG. 6 illustrates a control solution packet 66 according to another embodiment of the present invention. As shown, the control solution packet 66 has a container 36c in the form of a capsule 68 that defines a cavity 70 in which the control fluid 40 is contained. As mentioned above, the control fluid 40 can be pre-pressurized within the capsule 68 before calibration or can become pressurized during calibration. The capsule 68 is designed to be permeable by the piercing device 32 of the bodily fluid sample device 20. In one embodiment, the capsule 68 includes a gelatinous casing that surrounds the control fluid 40. In FIG. 6, the capsule 68 has an elliptical cross-sectional shape such that the capsule 68 has a generally semi-spherical shape. However, it is contemplated that the capsule 68 can have a different shape than is shown. By way of non-limiting example, the capsule 68 can have a spherical shape, a cylindrical shape, a cubic shape or a rectangular shape, to name a few.

As depicted, the capsule 68 has a capsule wall 72 with a thickness T. The thickness T of the capsule wall 72 depends on many factors including, but not limited to, the material composition of the capsule 68, the viscosity of the control fluid 40, the bodily fluid sampling device 20 and the pressure of the control fluid 40 within the capsule 68. In one form, the thickness T of the capsule wall is less than the penetration depth P of the piercing device 32 so as to allow the piercing device 32 to penetrate into the cavity 70 of the capsule 68. In one embodiment, the capsule 68 has a thickness of about 0.1 mm to about 10 mm. As should be appreciated, the capsule 68 is designed to be pierced by the piercing device 32 at different locations along the capsule wall 72. To reduce the risk that the piercing device 32 will penetrate the capsule wall 72 at two places, the capsule 68 has a minimum height H1 and minimum depth D1 that are sized to prevent double penetration of the capsule wall 72. In the illustrated embodiment, the minimum depth D1 of the capsule wall 72 is greater than the penetration depth P of the piercing device 32.

Figure 7:
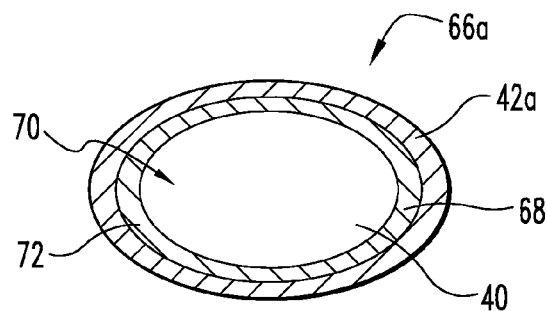
FIG. 7 is a cross-sectional view of a control solution packet according to another embodiment of the present invention.

In another embodiment illustrated in FIG. 7, the capsule 68 of control solution packet 66a is covered by membrane 42a. The membrane 42a provides added structural support to the control solution packet 66a, and also regulates the delivery of the control fluid 40 by sealing around the piercing device 32 as the control solution packet 66a is pierced. Moreover, the membrane 42a reduces leakage of control fluid 40 from around the piercing device 32. During calibration, if the compressive force exerted by the bodily fluid sampling device 20 excessively deforms the capsule 68, double penetration of the capsule wall 72 or over pressurization of the control fluid 40 can occur. The structural support provided by the membrane 42a helps to resist excessive deformation of the control solution packet 66a, and thus reduces the risk of double penetration of the capsule wall 72 or over pressurization.

Figure 8:
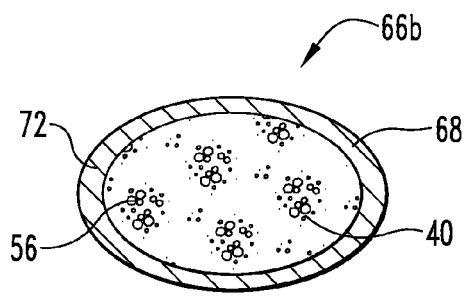
FIG. 8 is a cross-sectional view of a control solution packet according to a further embodiment of the present invention.

As shown in FIG. 8, a control solution packet 66b according to a further embodiment has a porous, sponge-like material 56 along with the control fluid 40 encapsulated within the capsule 68. The sponge/foam material 56 helps to support the overall shape of the capsule 68. Furthermore, the combination of material 56 and the control fluid 40 provide resistance to deformation of the capsule 68 during the piercing of the control solution packet 66b. Due to the porous nature of material 56, delivery of the control fluid 40 to the bodily fluid sampling device 20 is able to be regulated. The sponge/foam material 56 controls the depth of the penetration of the piercing device 32 and prevents the contamination of the bodily fluid sampling device 20 as well as eliminating contamination from the surrounding capsule walls 72. The structural support of the capsule 68 provided by material 56 prevents the piercing device 32 from penetrating entirely through the control solution packet 66b.

Figure 9:
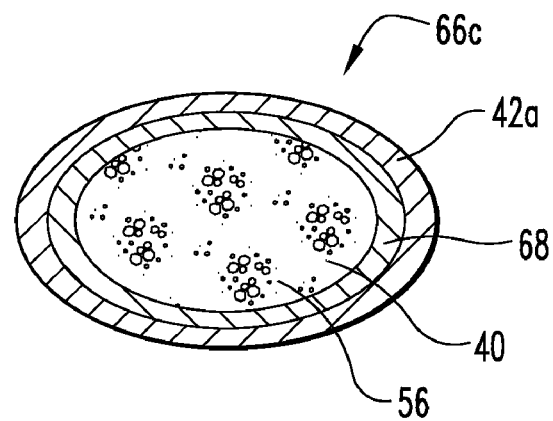
FIG. 9 is a cross-sectional view of a control solution packet according to another embodiment of the present invention.

FIG. 9 illustrates a control solution packet 66c according to another embodiment of the present invention. As shown, packet 66c includes capsule 68 containing both the control fluid 40 and the sponge/foam material 56. The capsule 68 is covered by membrane 42a. Together the membrane 42a and the sponge/foam material 56 provide structural support to the control solution packet 66c in order to resist over-penetration by the piercing device 32. In addition, the porous sponge/foam material 56 regulates delivery of the control fluid 40 to the bodily fluid sampling device 20. In one form, the control fluid 40 is pre-pressurized and has a viscosity that controls the amount of the control fluid 40 delivered to the bodily fluid sampling device 20. In another form, the control fluid 40 is stored within the capsule 68 at generally around ambient pressure and becomes pressurized when the bodily fluid sampling device 20 presses against the control solution packet 66c during calibration.

Figure 10:
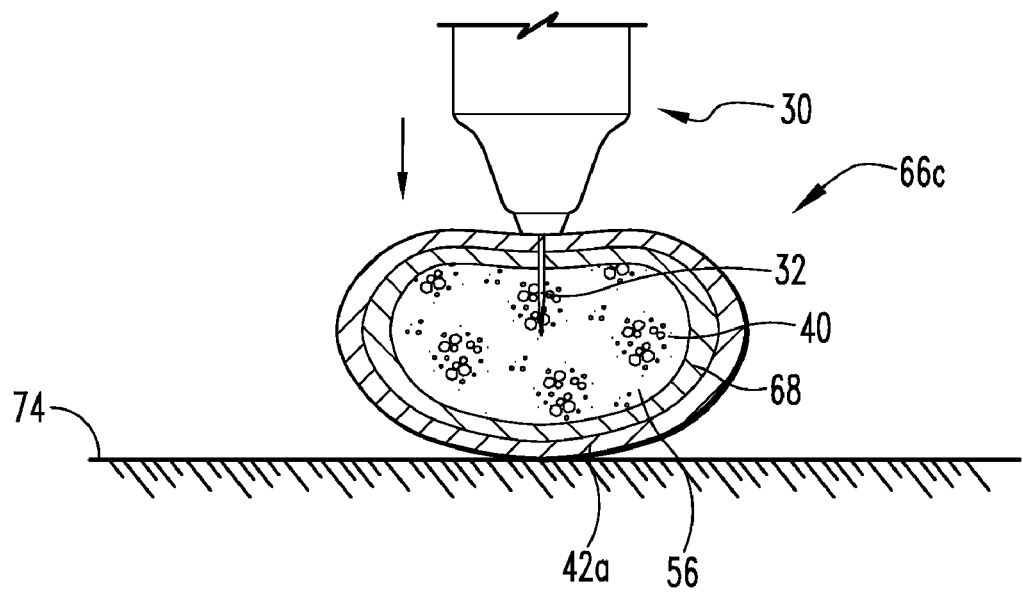
FIG. 10 is a partial, cross-sectional view of the FIG. 1 bodily fluid sampling device piercing the FIG. 9 control solution packet.

A technique for calibrating the bodily fluid sampling device with a control solution packet according to the present invention will now be described with reference to FIG. 10. For explanation purposes, the FIG. 9 control solution packet 66c has been illustrated in FIG. 10. It should be understood that this technique can be applied to the other types of control solution packets according to the present invention. As shown in FIG. 10, control solution packet 66c rests on a support surface 74. The bodily fluid sampling device 20 is placed in contact with the control solution packet 66c. The operator presses the bodily fluid sampling device 20 against the control solution packet 66c in order to compress the packet 66c and pressurize the control fluid 40 in the packet 66c. As discussed above, alternatively, the control solution packet 66c is prepressurized such that only slight to no pressure needs to be applied. Even when pre-pressurized, the control solution packet 66c can be further pressurized by compressing the packet 66c between the bodily fluid sampling device 20 and the support surface 74. The piercing device is then deployed so as to pierce through the membrane 42a and the capsule 68.

As shown in FIG. 10, both the sponge-foam material 56 and the membrane 42a resist the compressive force of the bodily fluid sampling device 20 so as to prevent over-deformation of the control solution packet 66c, which can lead to over-pressurization of the control fluid 40 and/or double penetration of the control solution packet 66c. The membrane 42a seals around the piercing device 32 in order to prevent leakage of the control fluid 40.

The pressure inside the control solution packet 66c forces the control fluid 40 up the piercing device 32 and into the test area 31 of the bodily fluid sampling device 20. The viscosity as well as the pressure of the control fluid 40 ensures that the required amount of the control fluid 40 is delivered to the test area 31 of the bodily fluid sampling device 20. The bodily fluid sampling device 20 takes a reading of the sampled control fluid 40 in the test area 31. The reading is displayed on the display device 24 of the bodily fluid sampling device 20. The displayed reading can be used to determine whether the bodily fluid sampling device 20 is properly calibrated. In one embodiment, the piercing device 32 is removed from the control solution packet 66c before the reading is taken. In another embodiment, the reading is taken while the piercing device 32 is inserted inside the control solution packet 66c.

Figure 11:
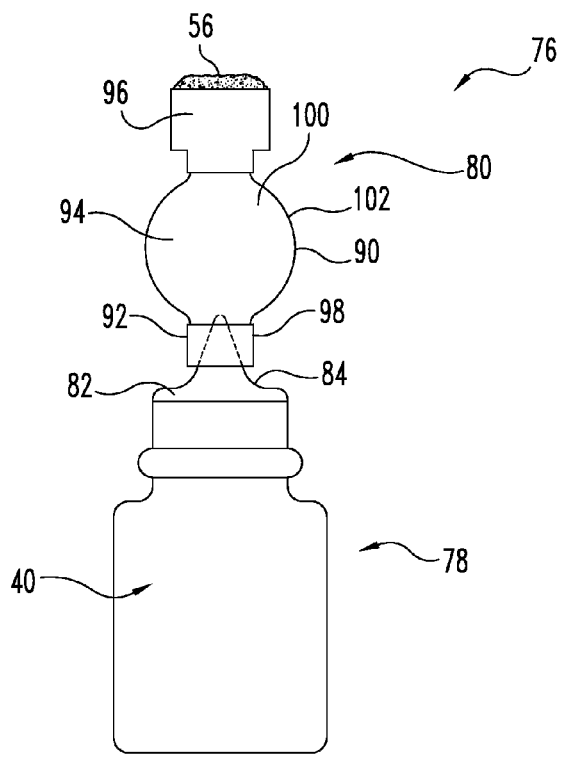
FIG. 11 is a front elevational view of a control solution bottle with a calibration fluid dosing attachment according to another embodiment of the present invention.
Figure 12:
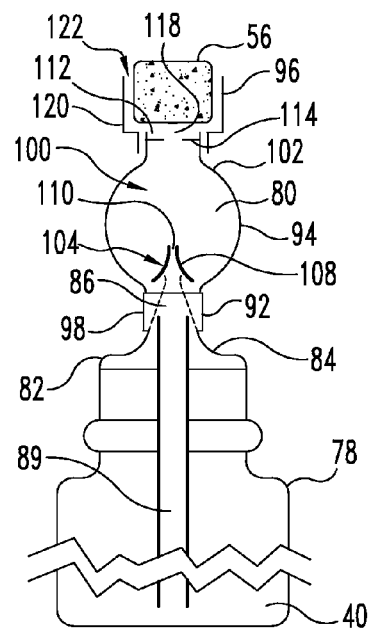
FIG. 12 is a partial, cross-sectional view of the FIG. 11 dosing attachment and bottle.

A calibration system 76 according to another embodiment of the present invention is illustrated in FIGS. 11-14. As shown in FIG. 11, the calibration system 76 includes a control solution bottle 78 and a dosing attachment or control solution packet 80 coupled to the bottle 78. The bottle 78 contains a control fluid 40 and has an outlet portion 82 for dispensing the control fluid 40. In one embodiment, the control solution bottle 78 is a standard control solution bottle that is configured to deliver drops of the control fluid 40 from the outlet portion 82. In the embodiment illustrated in FIG. 12, the outlet portion 82 has an elastic nipple 84 with an opening 86 that is used to administer the control fluid 40. A supply tube 88 extends into the outlet portion 82 so as to supply the control fluid 40 to the opening 86 in the nipple 84.

Referring again to FIG. 11, the dosing attachment 80 has a body 90 that includes a coupling portion 92, a collection portion 94 and a dispensing portion 96. As shown, the coupling portion 92 is fluidly coupled to the outlet portion 82 of the bottle 78 so that the dosing attachment 80 can receive control fluid 40 from the bottle 78. In one embodiment, the body 90 of the dosing attachment 80 is formed from plastic. However, it should be understood that the body 90 can be formed from other materials as would occur to those skilled in the art. In the illustrated embodiment, the coupling portion 92 includes a cylindrical tube 98 that is received around the opening 86 in the nipple 84. As should be appreciated, the tube 98 can have a different shape, besides cylindrical, in order to accommodate other types of outlet portions 82.

The collection portion 94 of the dosing attachment 80 defines a collection cavity 100 in which the control fluid 40 from the bottle 78 is collected. The collection cavity 100 has a specified volume so that a predefined dosage of the control fluid 40 is delivered to the dispensing portion 96. Walls 102 of the collection portion 94 are deformable such that the collection portion 94 can be compressed in order to deliver the control fluid 40 to the dispensing portion 96. In one form, the walls 102 of the collection portion 94 are made of a soft plastic. However, it should be appreciated that the collection portion 94 can be made from other types of materials. In the illustrated embodiment, the walls 102 of the collection portion 94 are shaped such that the collection portion 94 has an overall bulbous or spherical shape. It should be understood that the collection portion 94 can have an overall shape that is different from the one shown.

Figure 13:
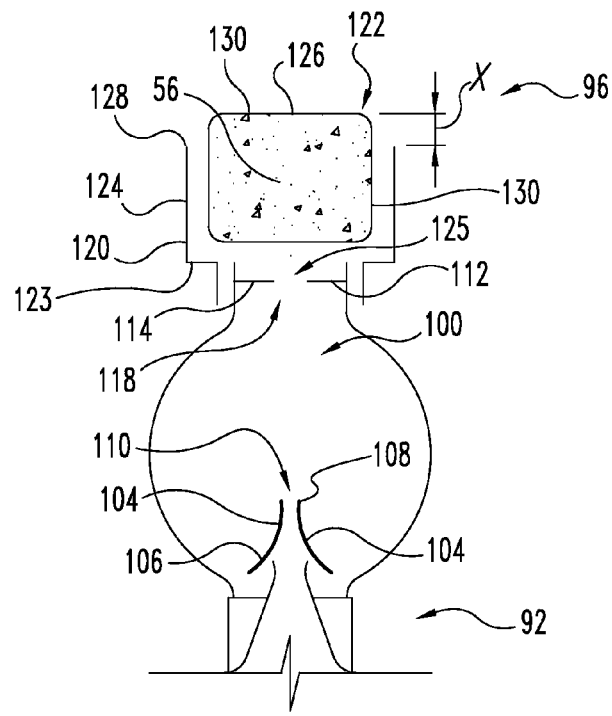
FIG. 13 is an enlarged, cross-sectional view of the FIG. 11 dosing attachment.

Between the coupling portion 92 and the collection cavity 100, the dosing attachment 80 has an inflow check valve 104 that allows the control fluid 40 to only flow in one direction into the collection cavity 100. The inflow check valve 104 prevents contamination of the control solution bottle 78 by preventing the control fluid 40 in the dosing attachment 80 from flowing back into the bottle 78. As shown in FIG. 13, the inflow check valve 104 includes a conical, elastic member 108 that defines an inflow opening 110 through which the control fluid 40 flows. The conical member 108 is received over the opening 86 in the nipple 84. When the control fluid 40 is pressurized in the cavity 100 through compression of the walls 102, the conical member 108 deforms so as to close the inflow opening 110. To prevent back flow from the dispensing portion 96, the dosing attachment 80 has an outflow check valve 112 positioned between the collection cavity 100 and the dispensing portion 96. In the illustrated embodiment, the outflow check valve 112 includes a disc-shaped valve member 114 that defines an outflow opening 118 through which the control fluid 40 flows to the dispensing portion 98. To prevent back flow of the control fluid 40, the disc-shaped valve member 114 is elastic in order to constrict flow through the outflow opening 118. As should be appreciated, check valves 104 and 112 can include other types of mechanisms for directing fluid flow as would occur to those skilled in the art.

As illustrated in FIG. 13, the dispensing portion 96 of the dosing attachment 80 includes a dispensing member 120 that defines a dispensing cavity 122 in which sponge/foam-like material 56 is disposed. The dispensing member 120 has an end wall 123 and sidewalls 124 that extend from the end wall 123 to cover the majority of the sponge-like material 56 so as to prevent the sponge-like material 56 from inadvertently dispensing control fluid 40 onto components of the fluid sampling device, which could lead to contamination of the sampling device. The end wall 123 supports the sponge-like material 56 during compression, and the end wall 123 defines a fluid passage 125 through which the control fluid 40 flows. As shown, a portion 126 of the sponge-like material 56 extends above contact edge 128 of the sidewalls 124. The portion 126 of the sponge-like material 56 extending above the contact edge 128 has a contact or dispensing surface 130 from which the control fluid 40 is dispensed during calibration. When measured from the edge 128 of the dispensing member 120 to the contacting surface 130 of the sponge-like material 56, portion 126 has a height X that is sized to deliver a predefined amount of control fluid 40 during calibration. The dispensing member 120 is configured to be received inside a fluid sampling device during calibration. In the illustrated embodiment, the dispensing member 120 has a generally cylindrical shape. However, as should be appreciated, the dispensing member 120 can be shaped differently in order to accommodate different types of fluid sampling devices.

Figure 14:
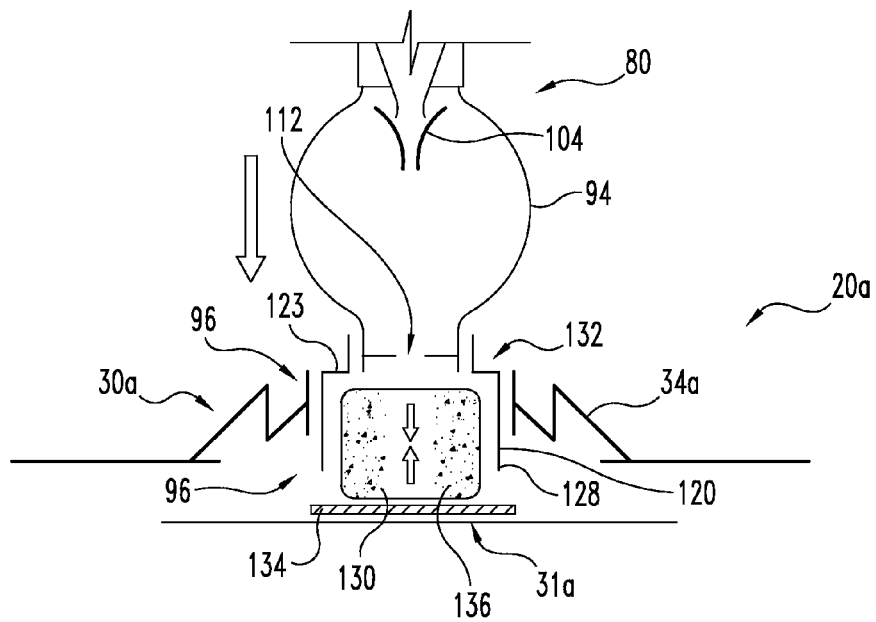
FIG. 14 is a partial, cross-sectional view of the FIG. 11 dosing attachment contacting a test area of a bodily fluid sampling device.

The above-described calibration system 76 can be used to calibrate a variety of types and/or styles of bodily fluid sampling devices. For example, a bodily fluid sampling device 20a that can be calibrated with the calibration system 76 is illustrated in FIG. 14. As depicted, the sampling device 20a includes a sampling system 30a with a deformable sampling cone 34a that defines a sample opening 132. The sampling device 20a further includes a test area 31a in which a bodily fluid sample is tested. In the illustrated embodiment, the test area 31a incorporates a test strip 134 that is used to collect the bodily fluid sample. As should be appreciated, other types of bodily fluid sample collection systems, besides test strips, can be used to collect the fluid sample. Although not illustrated, the sampling device 20a further includes a piercing device 32 of the type above described, which can be removed during calibration.

To calibrate the sampling device 20a with calibration system 76, the dosing attachment 80 is coupled to the control solution bottle 78 that contains the control fluid 40. The bottle 78 is squeezed until the collection cavity 100 is filled with the control fluid 40. After the collection cavity 100 is filled, the walls 102 of the collection cavity 100 are squeezed to deliver a predefined dosage of control solution 40 into the sponge-like material 56. In one embodiment, the dosing attachment 80 remains coupled to the bottle 78 as the collection portion 94 of the dosing attachment 80 is squeezed. As mentioned above, the inflow check valve 104 prevents control fluid 40 from flowing back into the bottle 78 when the collection portion 94 is squeezed. In an alternate embodiment, to ensure that none of the control fluid 40 in the collection cavity 100 flows back into the bottle 78, the dosing attachment 80 is first removed from the bottle 78 before the collection portion 94 is squeezed. The collection cavity 100 has a specified volume that limits the dosage of the control fluid 40 delivered to the sponge-like material 56 in order to ensure that the sponge-like material 56 is not over saturated. If the sponge-like material 56 became over saturated, control fluid 40 could drip from the sponge-like material 56 and contaminate the sampling device 20a.

In one embodiment, during calibration, the piercing device 32 is removed from the sampling device 20a to allow the dispensing portion 96 of the dosing attachment 80 gain access to the test area 31a. In another embodiment, the piercing device 32 is positioned or repositioned in the sampling device 20a to allow the dispensing portion 96 to gain access to the test area 31a. To distinguish between calibration readings and actual sample readings, the sampling device 20a can include a sensor that senses when the piercing device 32 has been removed or repositioned for calibration.

As shown in FIG. 14, the dispensing portion 96 of the dosing attachment is designed to be received through the sample opening 132 and contact the test strip 134. As mentioned above, the sidewalls 124 of the dispensing portion 96 prevent components, such as cone 34a, from being contaminated with the control solution 40 during calibration. The calibration system 76 is designed to calibrate the sampling device 20a from a variety of positions, such as from an upright position (FIG. 11) or an inverted position (FIG. 14).

The dispensing portion 96 can be inserted into the sampling device 20a before or after the sponge-like material 56 is wetted with the control fluid 40. As should be appreciated, when the sponge-like material 56 is wetted, the control fluid 40 is stored within pores 136 in the material 56. Once the dispensing portion 96 is inserted inside the sampling device 20a and the sponge-like material 56 is wetted, the dispensing surface 130 of the sponge-like material 56 is pressed against the test strip 134 until the contact edge 128 of the dispensing member 120 contacts the test strip 134. This ensures that the sponge-like material 56 is compressed a designated distance (X) to ensure the proper dosage of control fluid 40 is delivered to the test strip 134 for calibration. As should be appreciated, the control fluid 40 within the pores 136 of the sponge-like material 56 is pressurized when the material 56 is compressed, and due to this pressure, the control fluid 40 is dispensed from dispensing surface 130 onto the test strip 134.

After the control fluid 40 has been dispensed onto the test strip 134, the dispensing portion 96 of the dosing attachment 80 is removed from the sampling device 20a. The sampling device 20a can then test the control fluid 40 on the test strip 134 in order to determine if the sampling device 20a is properly calibrated. In one embodiment, the entire dosing attachment 80 is disposable such that after each use the dosing attachment 80 is discarded and replaced with a new one to ensure that the supplied control fluid 40 is not contaminated. In another embodiment, only the sponge-like material 56 is replaced after each use.

In this embodiment, the collection portion 94 has been described as being squeezed in order to provide the control solution to the dispensing portion 96. However, it is not necessary that the collection portion 94 be pressurized in order to provide the control solution, and alternative means such as a wicking or gravity feeding of the solution can also be used in appropriate situations to make the control solution available at the dispensing portion.

It is apparent from the foregoing description that the present invention provides a unique system for the delivery of a control solution to a sampling device for bodily fluids, particularly to an integrated sampling device. In contrast to the prior art, the present invention provides a system by which the control solution is presented to and acquired by the sampling device in the same manner in which the device would obtain the bodily fluid. The user of the sampling device therefore does not have to use an alternative technique, but rather can operate the device in the customary manner for sampling the bodily fluid.

Regarding the embodiments of FIGS. 1-10, the present invention provides a packet that provides the control solution to a sampling device which customarily acquires the bodily fluid through a hollow needle. In the normal operation of the sampling device used in this embodiment, the bodily fluid is acquired by inserting a hollow needle into the skin and allowing the fluid to pass up through the needle based on a pressure differential. The user similarly acquires the control solution in the same manner, by inserting the needle into the control solution packet and allowing the control solution to pass up through the needle based on a pressure differential. Thus, the user does not use a different technique for acquiring the bodily fluid or for acquiring the control solution.

In the embodiment of FIGS. 11-14, the same approach is again employed by the user of the sampling device for acquiring either the bodily fluid or the control solution. In conventional use of the sampling device, the user places the sampling device against the skin and the device produces and acquires the bodily fluid for testing. In the same manner, the sampling device is placed against the dispensing surface 130 of the sponge-like material 56. This dispensing surface is comparable to the user's skin in that the sampling device is pressed against the surface and an amount of control solution is thereafter acquired from the surface for testing. In the case of the bodily fluid, the sampling device may additionally function to lance the skin and thereby provide an incision site at which the bodily fluid may collect for sampling. The use of a wetted foam pad avoids the need for actual lancing of the pad to provide the control solution. However, the sampling device is still operated in the same fashion as when used to obtain bodily fluid, regardless of whether a lancet is used or not. Thus, the user again does not have to perform an alternative method in order to apply the control solution, but rather simply uses the sampling device in the fashion to which the user is accustomed for acquiring bodily fluid.

In the embodiment of FIGS. 11-14, it has been indicated that in one approach the lancet may be removed or displaced when the control solution is being acquired. However, it will be appreciated that a lancet may be maintained in the usual position, and may be advanced against the foam pad during the procedure for acquiring the control solution. The use of the lancet is not required when a foam pad is employed, but the action of the lancet also will not interfere with the functioning of the sampling device to acquire the control solution in accordance with the present invention. Therefore, in this manner there is no change required in the set-up or use of the sampling device when acquiring control solution in accordance with the present invention.

Figure 15A:
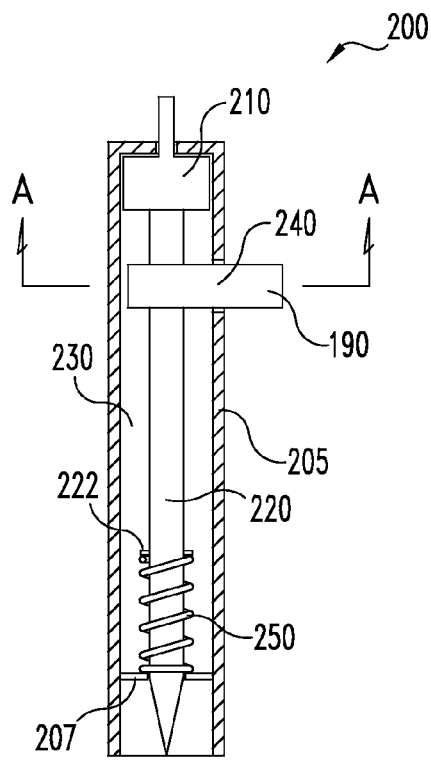
FIG. 15A is a cut-away side view of one apparatus according to a preferred embodiment of the present invention.
Figure 15B:
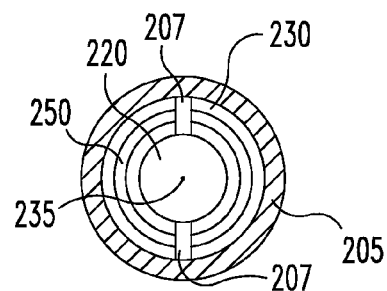
FIG. 15B is a bottom view of the apparatus of FIG. 15A.
Figure 15C:
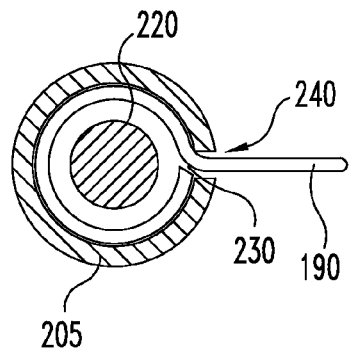
FIG. 15C is a cross-sectional view taken along line A-A of FIG. 15A illustrating a test strip disposed within the testing device.

In an alternative embodiment, illustrated in FIGS. 15A, 15B and 15C, the control solution packet is shown in use with another integrated sampling device which includes the lancing of the packet to obtain the control solution. The sampling device 200 in this example unit comprises a body 205 having associated features to facilitate the use of the unit. Body 205 is a capillary member having an internal diameter sized to draw and retain fluid from a contacted source using capillary action. Body 205 includes internal structure for supporting the lancet 220 and for moving the lancet longitudinally between a first, retracted position and a second, extended position. The unit 200 also includes means relating to the testing of the bodily fluid or control solution as described hereafter.

Referring to FIG. 15A in detail, there is shown a basic, integrated sampling unit 200 for testing bodily fluids. Device 200 comprises a main body 205, lancet 220 with distal point 235, biasing device 250, and lancet carrier or hub 210. Annular space or void 230 is defined within body 205 and disposed between the lancet 220 and the internal wall of main body 205. This space is generally referred to herein as an "annular" space, although it will be appreciated that the shape of the space will vary depending on the shapes of the lancet and capillary member and the position of the lancet within the capillary member.

For purposes herein, the term annular space includes generally the space between the capillary member and the contained lancet, including the variety of physical shapes that the space between the lancet and the capillary member may assume, depending at least in part on the noted possible variations. In certain embodiments, the annular space 230 between lancet 220 and main body 205 is between 10 and 500 µm, and is preferably between 20 and 200 µm to obtain optimal capillary fill time with blood.

Referring now to FIG. 15B there is shown a bottom view of device 200. FIG. 15B illustrates annular space 230 disposed between lancet 220 and main body 205. In use, the annular space 230 performs a capillary function in that bodily fluid is drawn up through apparatus 200 within annular space 230, with displaced air escaping from the unit through the opposing end of body 205. The body 205 and lancet or lancing element 220 are sized and arranged to provide the desired flow of bodily fluid through capillary action. This will depend to some extent on the subject bodily fluid, as well as on other parameters.

In addition, the flow of fluid may be enhanced by forming the lancing member and/or the interior surface of the capillary member from a material which is hydrophilic, which has been treated to be hydrophilic, or which has been coated with a hydrophilic material such as a surfactant or hydrophilic polymers. The surfaces can also be treated using polyamides, oxidation (e.g. corona/plasma treatment); plasma chemical vapor deposition; vacuum vapor deposition of metals, metaloxides or non-metaloxides; or deposition of an element which oxidizes with water. The annular space is therefore sized to provide the desired flow by capillary action with the various influences being taken into account.

The lancing element or lancet 220 is received and longitudinally movable within the capillary space 230 of unit 200 between a first, retracted position, and a second, extended position. Means are provided for resiliently extending and retracting the lancet in order to make a desired incision and to then withdraw the lancet back into a shielded position. Various means for extending a lancet relative to a housing are known in the art, and are useful in combination with the present invention. These devices, for example, typically include lancets held by carriers that are spring loaded for movement relative to the surrounding housing. Alternatively, a spring-loaded hammer may be use to impact the lancet carrier in order to drive it in the direction to lance the skin. Examples of such mechanisms are contained in the following U.S. Pat. Nos. 5,951,492; 5,857,983 and 5,964,718. The foregoing disclosures are incorporated herein by reference, and constitute a part of the description of the present invention and its available design alternatives.

These devices typically extend the lancet to a defined extent, such as by moving the lancet to a stop. Such devices frequently are produced with a predefined limit of travel for the lancet, thereby defining a penetration for the lancet into the skin. Alternatively, devices are well known which permit the user to adjust the penetration depth, such as by turning a wheel or other mechanism, with such adjustable devices frequently including a dial or other display which indicates the selected depth. These types of mechanisms are useful in combination with the present invention.

Various means may similarly be employed for retracting the lancet after it has made the incision, and many such mechanisms are known in the art, including the references previously cited and incorporated herein. One example of a retraction means is spring 250 (FIG. 15A) surrounding lancet 220 and disposed between bearing surfaces or retainers 207 associated with body 205 and bearing surfaces or retainers 222 associated with lancet 220. Preferably bearing surfaces 207 and 222 are fingers, tabs, flanges, rings, or similar structures which provide sufficient bearing surfaces to retain spring 250 in place without materially impeding capillary fluid flow.

The resilient means is mounted to provide relative movement to retract the lancet into the main body after making the incision. Preferably the resilient means, such as spring 250, is made from a biocompatible material, such as metal, plastic, elastic or a similar material known in the art, which does not react with the sample or interfere with the testing procedure. The resilient means may allow multiple uses if the unit is to be reused, or may be a disposable or one-use mechanism used with disposable or one-use embodiments of the unit.

The resilient means may be placed in various locations without affecting the operation of the unit. For example, the spring may be placed in the lower portion of the main body (FIG. 15A), in the upper portion of the main body, externally of the main body between the body and the lancet carrier or externally in an external structure holding the unit. In further alternate embodiments, the resilient means can be arranged to provide expansion or contraction force to move the lancet to its retracted position. Thus, the means for retracting the lancet may, for example, push or pull the lancet to the retracted position.

Referring now to FIG. 15C there is shown a cross-sectional view of apparatus 100 taken about line A-A of FIG. 15A. Apparatus 200 further includes a testing element, such as reagent test strip 190 and test strip holder 240. Test strip holder 240 is an opening or slot in the wall of body 205 allowing test strip 190 to be inserted into apparatus 200 and received within annular space 230 such that test strip 190 is disposed radially around lancet 220. Test strip 190 can be held in place during the lancet's movement as shown, or it can move longitudinally with lancet 220 during the lancet's extension and retraction, as shown in later embodiments. Either way, the capillary action of unit 200 draws the body fluid into annular space 230 so that the fluid contacts the test strip.

Figure 16A:
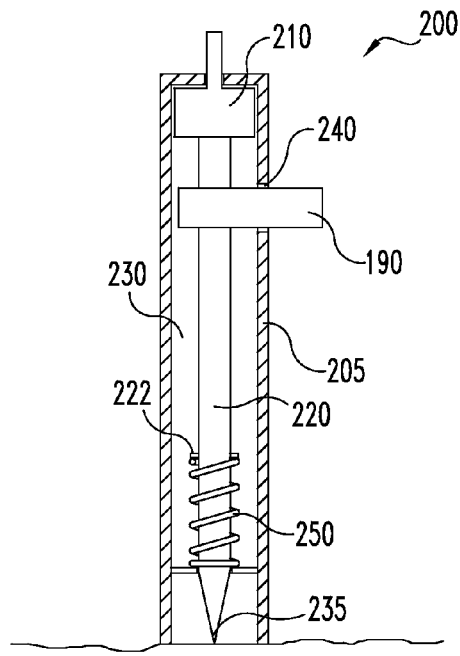
FIGS. 16A, 16B and 16C are cut-away side views of the apparatus of FIG. 15A in positions during use for obtaining bodily fluid.
Figure 16B:
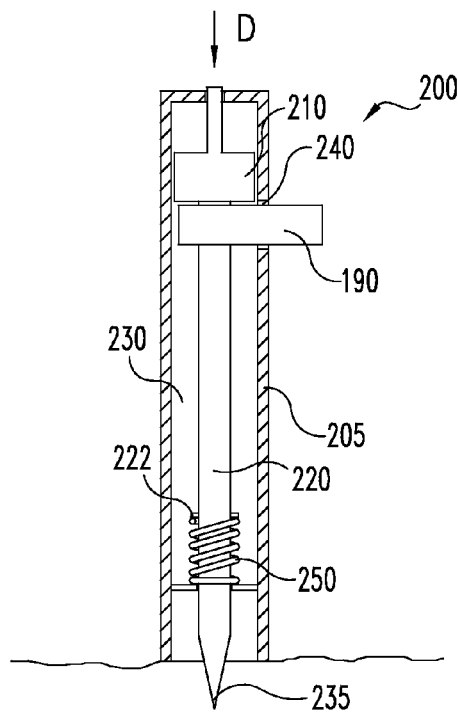
Figure 16C:
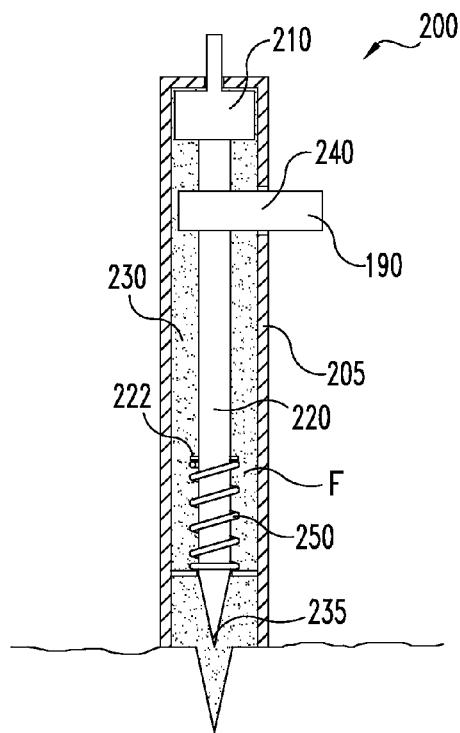

Illustrated in use for acquiring a bodily fluid in FIGS. 16A, 16B and 16C, the distal end of apparatus 200 is placed over an appropriate incision site, such as a forearm or fingertip such that the distal end abuts the skin surface. This provides a position control to enable application of a predetermined (chosen) pricking depth. In the retracted position, the distal tip 235 of the lancing element is fully received within the unit 200, preventing accidental contact with the tip. A downward force D (FIG. 16B) is then applied to lancet carrier 210, displacing lancet 220 from the static, protected position shown in FIG. 16A, to an extended position, shown in FIG. 16B. In the extended position, tip 235 of lancet 220 penetrates the skin tissue thereby creating a small incision, typically 0.5 to 1.2 mm deep. The incision depth will typically be pre-set at a desired level, or may be controlled by a selectable depth adjustment mechanism included on the unit.

The force D is then released from lancet carrier 210, and spring 250 biases lancet 220 into the retracted and protected position as shown in FIG. 16C. After retraction, apparatus 200 remains over the newly formed incision, preferably without movement, as shown in FIG. 16C, and bodily fluid F is drawn into annular space 230 of device 200 by capillary action. The capillary action is made more efficient since the capillary member is immediately in place and aligned with the incision, minimizing the concerns of movement or a gap between the tissue and the capillary member. A sufficient volume of bodily fluid F is drawn into annular space 230 so that it may be collected, tested and/or analyzed, for example by contact with test strip 190.

Testing of the fluid sample can be accomplished using standard optical or electro-chemical methods. The collected fluid can be analyzed using the full range of available procedures and equipment, including conventional test strip chemistries. For example, in one embodiment, after bodily fluid F contacts a micro-porous test strip 190, test strip 190 may be optically read in place or after removal to determine, for example, the blood glucose level. An optical reading of the test strip typically compares the color of the reaction of the test strip to a control chart. Alternately, test strip 190 may be removed from apparatus 200 and connected to or placed in a chemical or electronic testing apparatus. In a further alternate embodiment, unit 200 includes an optically-readable, reactive coating placed on the surface of lancet 220 or the interior circumference of body 250. Testing of bodily fluid F can be accomplished by the optical reading of the result of the reaction of the coating to the body fluid.

Figure 17:
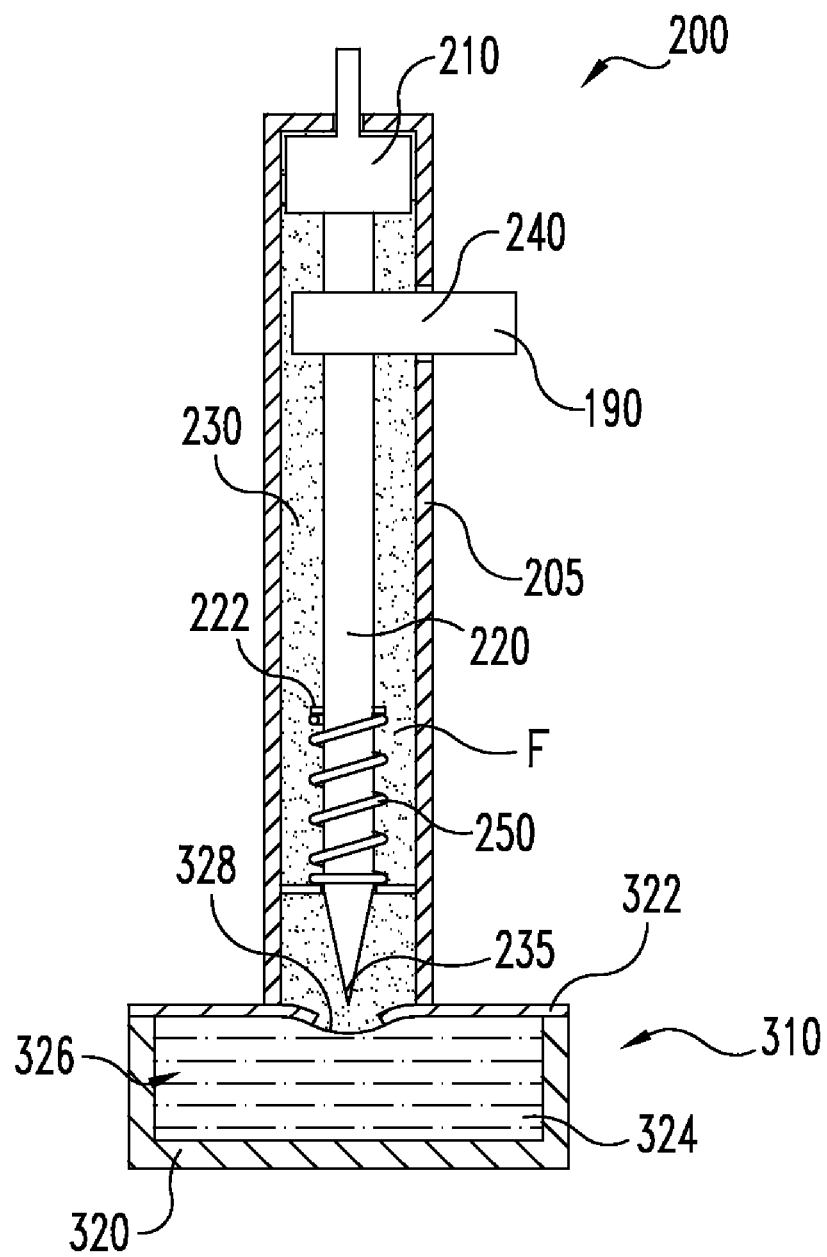
FIG. 17 is a cut-away side view of the apparatus of FIG. 15 shown in use for acquiring a control solution.

As shown in FIG. 17, the present invention provides an alternative form of control solution packet which again is useful with the sampling device in the same manner that the device functions to obtain the bodily fluid. The packet 310 comprises a body 320 and a thin membrane 322 extending over and sealed thereto. The control solution 324 is received within the container formed by the body 320 and membrane 322. A foam-like pad or other material 326 is optionally placed in the container. The sampling device is used with the control solution packet 310 in the same manner as described with respect to the sampling of bodily fluids. The sampling device is positioned against the membrane 322 and the piercing member is operated to pierce the membrane, thereby providing an opening 328 through which the control solution passes. As the control solution pools on top of the membrane, it is received by the capillary passageway 230 and moves up to the test strip 190 for analysis.

As for the previous embodiments, the control solution in the packet 310 may be under pressure or not, depending on the requirements of the sampling device. Although the sampling device is shown as being relatively large in the drawings for clarity, the size of the capillary passageway in this embodiment is such that a sufficient amount of control solution is readily formed on top of the membrane, even in the absence of pressure within the container. Sampling devices used for receiving bodily fluids frequently operate with very small amounts of fluid, and a sufficient amount of control solution is easily provided by the control solution packets of the present invention.

It is therefore an aspect of the present invention to provide a control solution packet that simulates the manner in which a sampling device acquires bodily fluid. The packet includes the control solution within a container, which corresponds to the bodily fluid contained within the body, such as the finger, earlobe, forearm, or the like. The acquires packet further includes a surface portion which simulates the skin. The sampling device the control solution from adjacent the surface portion, in the same manner that the sampling device acquires the bodily fluid from adjacent the skin. In one approach, the sampling device inserts a hollow needle through the skin or the surface portion to acquire the bodily fluid or control solution, respectively. In another embodiment, the sampling device lances the skin or surface portion and collects the resulting pool of bodily fluid or control solution, respectively. In a third approach, the control solution packet utilizes a foam pad that simulates the lanced skin, and which provides the pool of control solution upon pressing of the sampling device against the pad.

It will be seen that the various embodiments of the present invention provide a system for conveniently delivering a control solution to a sampling device for bodily fluids. The invention is particularly well suited to integrated sampling devices, such as integrated measurement devices, which comprise the functions of piercing the skin, transferring the bodily fluid from the skin to a test element, and generating a test result for a constituent or property of the bodily fluid. The present invention presents a control solution in a container that is brought into contact with the sampling device, which in a similar fashion produces a sample of control solution, acquires and transfers the control solution to the test element, and generates a test result for the control solution.

The present invention is distinguished from the prior art and provides several advantages. The control solution is not handled by the user in the manner of applying the solution to a test strip or other device which is then inserted into the test device. The test device instead handles the control solution. In addition, the present invention is advantageous in confining the control solution in a manner that inhibits spilling, splashing or contamination of the control solution, which can occur in prior art approaches.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for calibrating a bodily fluid sampling device, comprising:
   a porous material;
   a control solution bottle configured to hold an amount of control solution, the control solution being adapted to calibrate the bodily fluid sampling device;
   a coupling portion adapted to couple to the control solution bottle and receive the control solution from the bottle;
   a collection portion fluidly coupled to the coupling portion, the collection portion being adapted to collect the control solution from the bottle and deliver the control solution to the porous material, the collection portion has walls that define a collection cavity in which the control solution is collected, the walls of the collection portion are compressible for delivering the control solution to the porous material; and
   a dispensing portion fluidly coupled to the collection portion, the dispensing portion defining a cavity in which the porous material is received, wherein the porous material is compressible to pressurize the control solution and dispense the control solution to the bodily fluid sampling device when the porous material is compressed.

2. The apparatus of claim 1, wherein the coupling portion includes a cylindrical tube.

3. The apparatus of claim 1, further comprising:
   an inlet check valve provided between the coupling portion and the collection portion to minimize back flow of the control solution into the bottle; and
   an outlet check valve provided between the collection portion and the dispensing portion to minimize back flow of the control solution into the collection portion.

4. The apparatus of claim 1, wherein the dispensing portion has a contact edge and a portion of the porous material extends above the contact edge to control the amount of the control solution delivered to the bodily fluid sampling device.

5. A kit for testing body fluid, comprising:
   a body fluid testing device having a piercing device and a device for sampling fluid to be tested, wherein said piercing device and said device for sampling fluid to be tested are integrated into a housing;
   a porous material for holding calibration fluid;
   a container that contains a control fluid, wherein the container includes a dosing attachment, the dosing attachment including a coupling portion, a collection portion, and a dispensing portion;
   wherein the coupling portion is adapted to couple to a control fluid bottle and receive the control fluid from the bottle;

wherein the collection portion is fluidly coupled to the coupling portion, the collection portion being adapted to collect the control fluid from the bottle and deliver the control fluid to the porous material, the collection portion has walls that define a collection cavity in which the control fluid is collected, the walls of the collection portion are compressible for delivering the control fluid to the porous material; and wherein the dispensing portion is fluidly coupled to the collection portion, the dispensing portion defining a cavity in which the porous material is received.

6. The kit according to claim 5, wherein the coupling portion includes a cylindrical tube.

7. The kit according to claim 5, further comprising:
an inlet check valve provided between the coupling portion and the collection portion to minimize back flow of the control fluid into the bottle; and
an outlet check valve provided between the collection portion and the dispensing portion to minimize back flow of the control fluid into the collection portion.

8. The kit according to claim 5, wherein the dispensing portion has a contact edge and a portion of the porous material extends above the contact edge to control the amount of the control fluid delivered to the bodily fluid sampling testing device.

* * * * *